US007967761B2

(12) United States Patent
Smith

(10) Patent No.: US 7,967,761 B2
(45) Date of Patent: Jun. 28, 2011

(54) SENSOR AND GUIDE WIRE ASSEMBLY

(75) Inventor: Leif Smith, Uppsala (SE)

(73) Assignee: Radi Medical Systems AB, Uppsala (SE)

(*) Notice: Subject to any disclaimer, the term of this patent is extended or adjusted under 35 U.S.C. 154(b) by 143 days.

(21) Appl. No.: 11/607,120

(22) Filed: Dec. 1, 2006

(65) Prior Publication Data

US 2008/0132806 A1 Jun. 5, 2008

(51) Int. Cl.
*A61B 5/00* (2006.01)

(52) U.S. Cl. ........................................ 600/585

(58) Field of Classification Search .................. 600/585, 600/437, 454, 467, 505

See application file for complete search history.

(56) References Cited

U.S. PATENT DOCUMENTS

| | | | | |
|---|---|---|---|---|
| 1,344,758 | A | 6/1920 | Donnelly | |
| 4,463,336 | A | 7/1984 | Black et al. | |
| 5,029,479 | A | 7/1991 | Bryan | |
| 5,132,658 | A | 7/1992 | Dauenhauer et al. | |
| 5,226,423 | A | 7/1993 | Tenerz et al. | |
| RE35,648 | E | 11/1997 | Tenerz et al. | |
| 6,106,476 | A * | 8/2000 | Corl et al. | 600/486 |
| 6,112,598 | A | 9/2000 | Tenerz et al. | |
| 6,167,763 | B1 | 1/2001 | Tenerz et al. | |
| 6,182,513 | B1 | 2/2001 | Stemme et al. | |
| 6,245,026 | B1 * | 6/2001 | Campbell et al. | 600/549 |
| 6,279,402 | B1 | 8/2001 | Fisher | |
| 6,312,380 | B1 * | 11/2001 | Hoek et al. | 600/437 |
| 6,343,514 | B1 | 2/2002 | Smith | |
| 6,461,301 | B2 | 10/2002 | Smith | |
| 6,495,908 | B2 | 12/2002 | Yang et al. | |
| 6,575,623 | B2 * | 6/2003 | Werneth | 374/179 |
| 6,615,067 | B2 | 9/2003 | Hoek et al. | |
| 6,692,446 | B2 | 2/2004 | Hoek | |
| 7,011,636 | B2 * | 3/2006 | Tenerz | 600/585 |
| 7,343,811 | B2 | 3/2008 | Tenerz et al. | |
| 2002/0013527 | A1 | 1/2002 | Hoek et al. | |
| 2003/0018273 | A1 | 1/2003 | Corl et al. | |
| 2003/0028128 | A1 | 2/2003 | Tenerz | |
| 2004/0068203 | A1 * | 4/2004 | Gellman et al. | 600/587 |
| 2004/0225232 | A1 | 11/2004 | Malmborg et al. | |

(Continued)

FOREIGN PATENT DOCUMENTS

EP 1 530 028 A1 5/2005

(Continued)

OTHER PUBLICATIONS

C. Li et al., "Polymer Flip-Chip Bonding of Pressure Sensors on Flexible Kapton Film for Neonatal Catheters," Proceedings of IEEE, Oct. 24-27, 2004, pp. 749-752.

(Continued)

*Primary Examiner* — Max Hindenburg
*Assistant Examiner* — Fangemonique Smith
(74) *Attorney, Agent, or Firm* — Foley & Lardner LLP

(57) ABSTRACT

A sensor and guide wire assembly (21; 41; 61; 81) for intravascular measurements of a physiological variable in a living body includes a sensor element (22; 42; 62; 82) mounted at a distal sensor portion (23; 43; 63; 83) of a guide wire (24; 44; 64; 84), wherein the sensor portion exhibits a maximal cross-sectional dimension which is larger than a maximal cross-sectional dimension of guide wire portions (28, 30; 48, 50; 68, 70) located proximally of the sensor portion.

19 Claims, 2 Drawing Sheets

U.S. PATENT DOCUMENTS

| | | | | |
|---|---|---|---|---|
| 2005/0000294 | A1 | 1/2005 | Tenerz et al. | |
| 2005/0011272 | A1 | 1/2005 | Tenerz | |
| 2005/0268724 | A1 | 12/2005 | Tenerz | |
| 2006/0079740 | A1 * | 4/2006 | Silver et al. | 600/309 |
| 2006/0207335 | A1 | 9/2006 | Tenerz et al. | |
| 2007/0078318 | A1 * | 4/2007 | Kling et al. | 600/323 |

FOREIGN PATENT DOCUMENTS

| | | |
|---|---|---|
| EP | 1 479 407 B1 | 3/2006 |

OTHER PUBLICATIONS

Sauser et al., "Pressure Microsensing Catheters for Neonatal Care," Sensors, Proceedings of IEEE, Oct. 24-27, 2004; pp. 1476-1479.

L. Smith, U.S. PTO Non-Final Office Action, U.S. Appl. No. 11/359,761, dated Apr. 20, 2007, 9 pgs.

L. Smith, U.S. PTO Notice of Allowance, U.S. Appl. No. 11/359,761, dated Nov. 7, 2007, 4 pgs.

* cited by examiner

SENSOR AND GUIDE WIRE ASSEMBLY

FIELD OF THE INVENTION

The invention relates generally to a sensor mounted in a distal portion of a guide wire for intravascular measurements of physiological variables in a living body, and in particular to the design of said distal portion.

BACKGROUND OF THE INVENTION

Sensor and guide wire assemblies in which a sensor, adapted for measurements of physiological variables in a living body, such as blood pressure and temperature, is mounted at a distal portion of a guide wire are known.

For example, the U.S. Pat. No. Re. 35,648, which is assigned to the present assignee, discloses a sensor and guide wire assembly comprising a sensor element, an electronic unit, signal transmitting cables connecting the sensor element to the electronic unit, a flexible tube having the signal cables and the sensor element disposed therein, a solid metal wire, and a coil attached to the distal end of the solid wire. The sensor element comprises a pressure sensitive device, e.g. a membrane, with piezoresistive elements electrically connected in a Wheatstone bridge-type of circuit arrangement mounted thereon. The entire contents of the '648 patent are incorporated herein by reference for additional details of equipment, methods, and techniques for such measurements.

The sensor element is usually provided in the form of a silicon chip, which besides the pressure sensitive device also comprises integrated electronic circuits. For various reasons it is desired to include ever more functionality in the electronic circuits. This need has so far been met by the general miniaturization trend that exists in the chip technology, which allows more functionality and more complex circuits to be integrated in a comparatively smaller area, or, in the three-dimensional case, in a smaller volume. Such miniaturization is extremely important within the field of guide wire mounted sensors, because the outer diameter of the sensor guide wire is in practice limited by the inner diameter of a catheter which in a so-called PCI (Percutan Coronar Intervention) is used for the treatment of a stenosis present in a blood vessel and which is threaded over the sensor guide wire and advanced to the site of interest. The standard inner diameter of such catheters is 0.35 mm (0.014 inches); and consequently the standard outer diameter of most guide wires, and in particular of sensor guide wires, is therefore 0.35 mm (0.014 inches).

However, the miniaturization of electronic circuits and chips is a difficult task, and it is far from certain that the chips industry can provide sensor chips which fulfil the future requirements for mounting in a guide wire adapted for intravascular measurements.

Consequently, there is a need for a guide wire design that provides more space for a sensor element, while at the same time allows use together with a standard catheter.

SUMMARY OF THE INVENTION

Embodiments of the present invention are directed to a sensor and guide wire assembly comprising a sensor element which is mounted in a distal portion of a guide wire. According to embodiments of the invention, a distal portion is provided which has a larger diameter than the rest of the guide wire, to thereby provide more space for the sensor element. The inventor has observed that a catheter very rarely (or never) is advanced over the distal tip of the guide wire, and has realized that a distal portion of a guide wire can have a larger diameter than the rest of the guide wire. A hollow distal portion having a larger diameter provides more space for a sensor element (and/or other devices) mounted within this distal portion.

According to the different embodiments disclosed below, an enlarged distal sensor portion can include the entire distal end of the sensor guide wire, but can also be restricted to the sensor portion, with the short distal end portion of the guide wire being smaller than the enlarged sensor portion.

Further, the sensor and guide wire assembly can be of a relatively well-known design (see, e.g., the above-referenced Re 35,648), with electrical leads that extend along the length of the guide wire and connect the sensor element to a male connector at the proximal end of the sensor guide wire; or the sensor and guide wire assembly can be of a wireless type, in which the sensor element wirelessly communicates with an external unit. Especially in the latter case, there is a need for very complex electronics and therefore a need for more space within the guide wire.

DETAILED DESCRIPTION OF PREFERRED EMBODIMENTS

Figure 1:
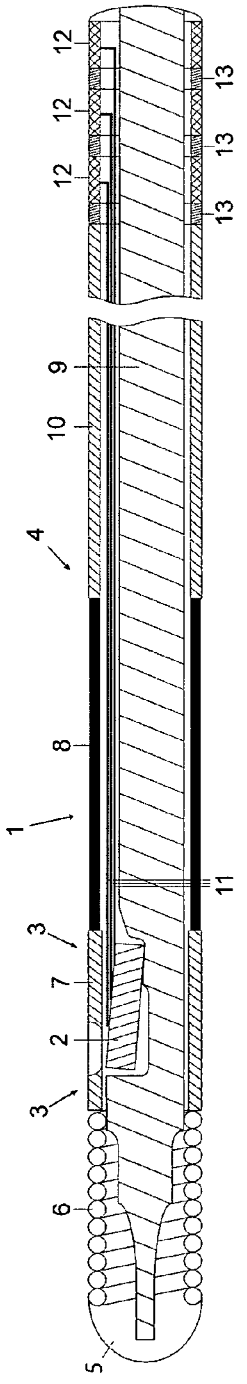
FIG. 1 is a schematic illustration of a sensor and guide wire assembly according to the prior art.

FIG. 1 illustrates schematically the general design of a sensor and guide wire assembly 1 according to the prior art. The sensor and guide wire assembly 1 comprises a sensor element 2, which is arranged in a distal portion 3 of a sensor guide wire 4. More specifically, the sensor guide wire 4 comprises a distal tip 5, a distal coil spring 6, a jacket or sleeve 7, a flexible distal tube 8, which also could be in the form of a coil spring, a core wire 9, and a proximal tube 10. The distal coil spring 6 is attached to the distal tip 5, and extends to the jacket 7, which serves as a housing for the sensor element 2. The flexible distal tube 8 extends between the jacket 7 and the proximal tube 10. The sensor element 2 is mounted in a recess in a distal portion of the core wire 9, and is through a window in the jacket 7 in fluid communication with the medium, e.g. blood, surrounding the sensor and guide wire assembly 1. The sensor and guide wire assembly 1 comprises further a number of signal transmitting cables 11, the distal ends of which are electrically connected to the sensor element 2 and which extend along the core wire 9 to the proximal end portion of the sensor guide wire 4, where each signal transmitting cable 11 is electrically connected to a conductive member 12. The conductive members 12 are electrically insulated from the core wire 9 as well as from each other by insulating members 13, so as to form a male connector adapted for connection to a corresponding female connector of an external signal conditioning and display unit (not shown in FIG. 1) for displaying the measured quantities, e.g. pressure, temperature and/or flow.

From FIG. 1, which is intended to present the essential elements of a sensor and guide wire assembly according to prior art, it may be appreciated that there is only a limited amount of space available for the sensor element. Throughout the present specification, the term "sensor element" as applied to pressure measurement is meant to encompass both the pressure sensitive member, e.g. a membrane, as well as the electronic components and circuits that are connected to the pressure sensitive member. It is even contemplated that a sensor element comprises a pressure sensitive part and an electronic part, which are connected by at least one electrical lead. The latter arrangement is disclosed in the U.S. patent application Ser. Nos. 11/063,744 and 11/359,761, both of which are assigned to the present assignee and whose entire contents are incorporated herein by reference for additional details of equipment, methods, and techniques for such arrangements. In a preferred embodiment of these patent applications, the pressure sensitive member and the electronic circuitry are incorporated in a silicon chip with integrated circuits.

Figure 2:
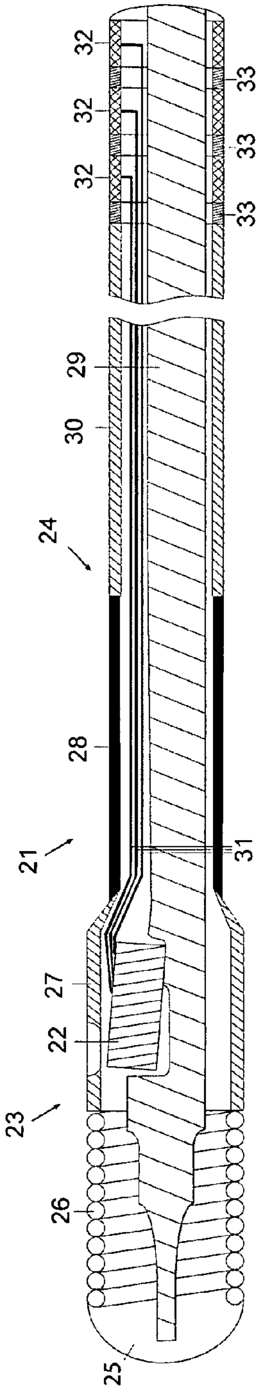
FIG. 2 shows a cross-sectional view of a first embodiment of a sensor and guide wire assembly according to the present invention.

A first embodiment of a sensor and guide wire assembly 21 according to the present invention is disclosed in FIG. 2, which illustrates that the sensor and guide wire assembly 21 comprises a sensor element 22, which is arranged in a distal portion 23 of a sensor guide wire 24. More specifically, the sensor guide wire 24 comprises a distal tip 25, a distal coil spring 26, a jacket or sleeve 27, a flexible distal tube 28, a core wire 29, and a proximal tube 30. The distal coil spring 26 is attached to the distal tip 25, and extends to the jacket 27, which serves as a housing for the sensor element 22. The flexible distal tube 28, which also could be in the form of a coil spring, extends between the jacket 27 and the proximal tube 30. The sensor element 22 is mounted in a recess in a distal portion of the core wire 29, and is through a window in the jacket 27 in fluid communication with the medium, e.g. blood, surrounding the sensor and guide wire assembly 21. The sensor and guide wire assembly 21 comprises further a number of signal transmitting cables 31, the distal ends of which are electrically connected to the sensor element 22 and which extend along the core wire 29 to the proximal end portion of the sensor guide wire 24, where each signal transmitting cable 31 is electrically connected to a conductive member 32. The conductive members 32 are electrically insulated from the core wire 29 as well as from each other by insulating members 33, so as to form a male connector adapted for connection to a corresponding female connector of an external signal conditioning and display unit (not shown in FIG. 2).

A comparison between FIG. 1 and FIG. 2 reveals that the sensor guide wire 24 shown in FIG. 2 is provided with a jacket 27 which is enlarged in comparison with the corresponding jacket 7 of the sensor guide wire 4 illustrated in FIG. 1. The enlargement of the jacket 27 provides more space for the sensor element 22 (and/or other devices), which consequently can comprise more electrical components and more complex functionality. In the first embodiment illustrated in FIG. 2, the jacket 27 is not the only portion of the sensor guide wire 24 that has a diameter which is enlarged in comparison with the diameters of the more proximal portions of the sensor guide wire 24. As can be seen, the diameters of the distal tip 25 and the distal coil spring 26 are also larger than the diameters of the flexible distal tube 28 and the proximal tube 30. In other words, in this embodiment, an enlarged distal sensor portion 23 encompasses the distal tip 25, the distal coil spring 26 and the jacket 27, and constitutes the extreme distal portion of the sensor guide wire 24. By making the diameter of the distal coil spring 26 equal to the diameter of the jacket 27 the assembly of the sensor and guide wire assembly 21 is simplified, because it is relatively easy to fit the distal coil spring 26 to the jacket 27 and to match the mechanical characteristics of these two elements to each other as there is no abrupt transition from the jacket 27 to the distal coil spring 26.

Figure 3:
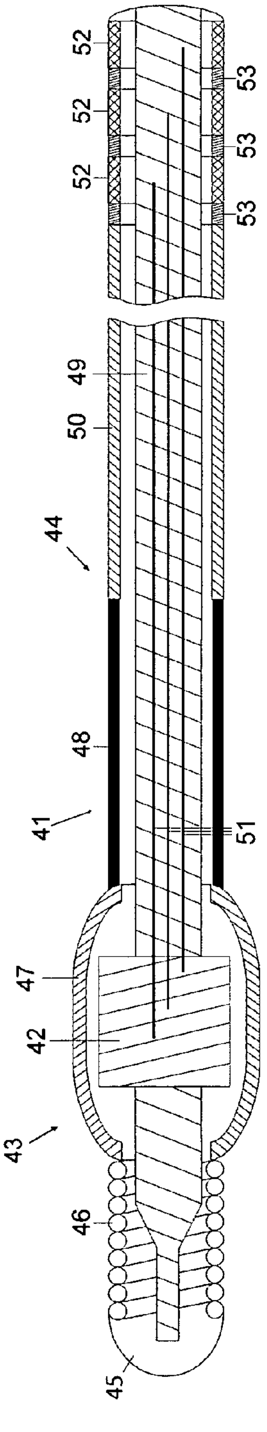
FIG. 3 shows a cross-sectional view of a second embodiment of a sensor and guide wire assembly according to the present invention.

FIG. 3 illustrates a second, alternative embodiment of a sensor and guide wire assembly 41 according to the present invention, and shows that the sensor and guide wire assembly 41 comprises a sensor element 42, which is arranged in a distal portion 43 of a sensor guide wire 44. More specifically, the sensor guide wire 44 comprises a distal tip 45, a distal coil spring 46, a jacket or sleeve 47, a flexible distal tube 48, a core wire 49, and a proximal tube 50. The distal coil spring 46 is attached to the distal tip 45, and extends to the jacket 47, which serves as a housing for the sensor element 42. The flexible distal tube 48, which also could be in the form of a coil spring, extends between the jacket 47 and the proximal tube 50. The sensor element 42 is mounted at a distal portion of the core wire 49, and is through a window (not visible in FIG. 3) in the jacket 47 in fluid communication with the medium, e.g. blood, surrounding the sensor and guide wire assembly 41. The sensor and guide wire assembly 41 comprises further a number of signal transmitting cables 51, the distal ends of which are electrically connected to the sensor element 42 and which extend along the core wire 49 to the proximal end portion of the sensor guide wire 44, where each signal transmitting cable 51 is electrically connected to a conductive member 52. The conductive members 52 are electrically insulated from the core wire 49 as well as from each other by insulating members 53, so as to form a male connector adapted for connection to a corresponding female connector of an external signal conditioning and display unit (not shown in FIG. 3).

In contrast to the first embodiment depicted in FIG. 2, the jacket 47 constitutes the only portion of the sensor guide wire 44 that has an enlarged diameter; and in particular the distal tip 45 and the distal coil spring 46 have both a diameter that is equal to the diameter of the flexible distal tube 48 and the proximal tube 50. Due to its small diameter, the distal end portion (i.e. the coil spring 46) of the sensor guide wire 44 can be made very flexible, which can be advantageous in some medical applications, such as when the sensor guide wire is manoeuvred through extremely tortuous vessels.

Figure 4:
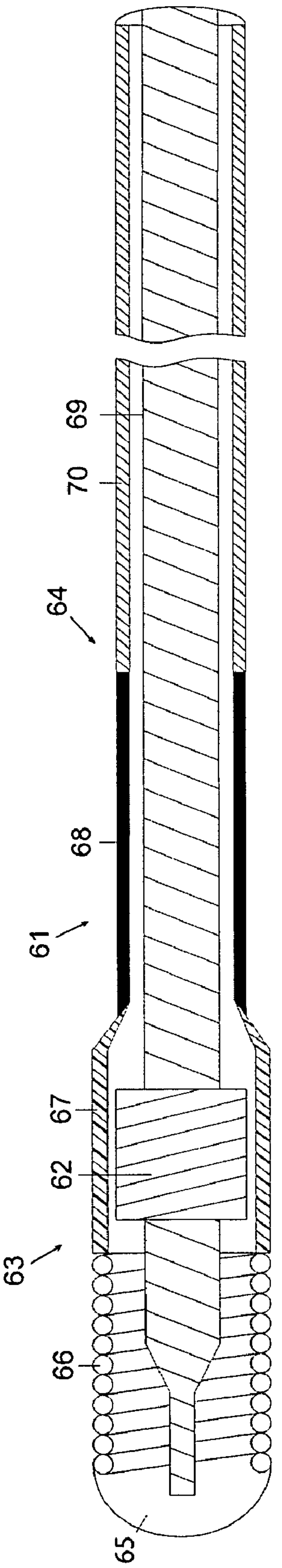
FIG. 4 shows a cross-sectional view of a third embodiment of a sensor and guide wire assembly according to the present invention.

As was briefly mentioned above, it is foreseen that a sensor element can communicate wirelessly with an external unit. In this case, the physical requirements put on the sensor element are considerably higher than in the wired case, because the sensor element must be able to receive energy via electromagnetic signals and communicate signals that are modulated in accordance with the sensed measurements. A schematic illustration of a wireless sensor and guide wire arrangement is shown in FIG. 4. In this third embodiment of the present invention, a sensor and guide wire assembly 61 comprises a sensor element 62, which is arranged in a distal portion 63 of a sensor guide wire 64. More specifically, the sensor guide wire 64 comprises a distal tip 65, a distal coil spring 66, a jacket or sleeve 67, a flexible distal tube 68, a core wire 69, and a proximal tube 70. The distal coil spring 66 is attached to the distal tip 65, and extends to the jacket 67, which serves as a housing for the sensor element 62. The flexible distal tube 68, which also could be in the form of a coil spring, extends between the jacket 67 and the proximal tube 70. The sensor element 62 is mounted to a distal portion of the core wire 69, and is through a window (not visible in FIG. 4) in the jacket 67 in fluid communication with the medium, e.g. blood, surrounding the sensor and guide wire assembly 61.

The third embodiment discussed in conjunction with FIG. 4 differs from the first and second embodiments of the present invention shown in FIG. 2 and FIG. 3, respectively, in that there are no signal transmitting cables provided. The sensor element 62 is instead capable of communicating with an external unit by electromagnetic signals, i.e. there is a wireless communication between the sensor element 62 and the external unit (not shown in FIG. 4). In this case, the physical requirements put on a sensor element are considerably higher than in the wired case, since the sensor element must be able to receive energy from some type of carrier signals and then communicate signals that are modulated in accordance with the sensed measurement. Other types of wireless communications are also possible, e.g. that the sensor is powered by a battery and only output signals are received by an external unit. Generally, the more functionality that is incorporated in a sensor element, the larger is the space required for the electronic circuits; and a sensor guide wire that provides a larger space for the sensor element is particularly advantageous for a wireless sensor and guide wire assembly.

Figure 5:
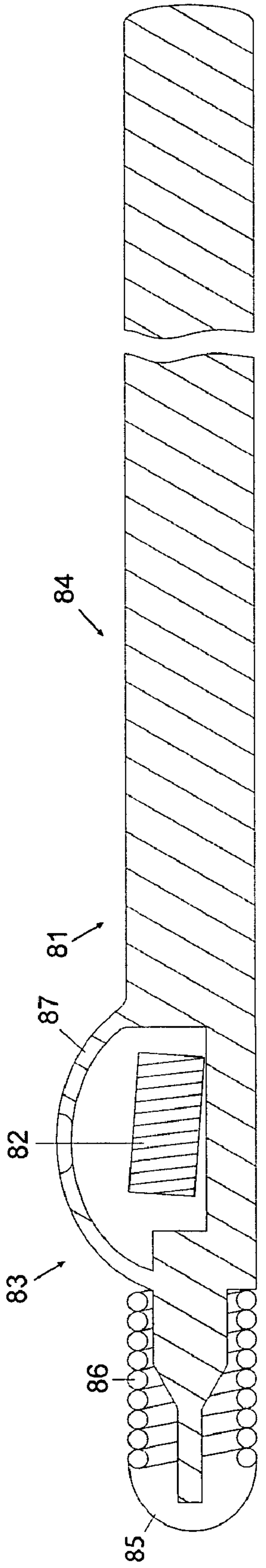
FIG. 5 shows a cross-sectional view of a fourth embodiment of a sensor and guide wire assembly according to the present invention.

In the third embodiment of FIG. 4, the general structure of the sensor guide wire 64 is the same as in the first and second embodiments, i.e. the sensor guide wire 64, like sensor guide wires 24 and 44, respectively, comprises a core wire as well as proximal and distal tubes. When a wireless sensor element is used, the design of a sensor guide wire can be significantly changed, due to the fact that signal transmitting cables can be dispensed with. In a fourth embodiment of the invention, which is schematically illustrated in FIG. 5, a sensor and guide wire assembly 81 adapted for wireless communication comprises a sensor element 82, which is arranged in a distal portion 83 of a sensor guide wire 84. More specifically, the sensor guide wire 84 comprises a distal tip 85, a distal coil spring 86, and a housing 87. The distal coil spring 86 is attached to the distal tip 85, and extends to the housing 87, in which the sensor element 82 is disposed. In this embodiment, it should be noted that there is no separate core wire and no proximal tube, as the sensor guide wire 84 is made from a solid wire, typically a metal wire. Further, the housing 87 is formed integrally with the solid wire that constitutes the sensor guide wire 84, and it can furthermore be noted that the housing 87 only projects out from a part of the circumference of the sensor guide wire 84. With this design, the mechanical characteristics of the sensor guide wire 84 can be improved, e.g. regarding torsional rigidity and bending stiffness.

As already has been discussed, the present invention is based on the observation that a catheter which is threaded onto a sensor guide wire never is advanced over the distal end of the sensor guide wire, and an enlarged distal sensor portion will consequently not prevent an effective use of a combination of a sensor guide wire and a catheter. As the person skilled in the art will recognize, there is a significant difference between a (sensor) guide wire and a catheter, for example, in that a catheter completely lacks steering capability, i.e. the catheter must be guided to the site of interest by means of a guide wire. For a standard sensor guide wire having an outer diameter of 0.35 mm (0.014 inches), which corresponds to the inner diameter of a standard catheter, the enlarged sensor portion is preferably less than 2 mm, and in particular less than 1 mm. The enlarged portion may be, for example, 10% larger (or 25%, or 50%, or 100% larger) than the non-enlarged portion.

Although the present invention has been described with reference to specific embodiments, also shown in the appended drawings, it will be apparent for those skilled in the art that many variations and modifications can be done within the scope of the invention as described in the specification and defined with reference to the claims below. It should in particular be noted that a sensor portion that is enlarged in comparison with the more proximal portions of a sensor guide wire can be symmetrical, i.e. having a larger diameter than the diameters of the more proximal portions but with the same centre, or can be asymmetric or non-circular, i.e. where only a sector of the cross-section has a larger radius than the more proximal portions, an example of which was illustrated in conjunction with FIG. 5, the important feature being that the sensor portion exhibits a maximal cross-sectional dimension that is larger than the maximal cross-sectional dimension of the guide wire portions located proximally of the sensor portion. Said cross-sectional dimension should be taken perpendicular to the central axis of the sensor guide wire. Consequently, the corresponding relationship and definition applies also for a distal end portion being smaller than the enlarged sensor portion, an example of which was discussed in conjunction with FIG. 3.

What is claimed is:

1. A sensor and guide wire assembly for intravascular measurement of a physiological variable in a living body, comprising:

a guide wire comprising an external contour, wherein a housing forms a portion of the external contour at a distal sensor portion of the guide wire; and a fluid pressure sensor element encompassed by the housing and at a radially internal location of the housing at the distal sensor portion, wherein the housing comprises a window for establishing fluid communication between the sensor element and a medium surrounding the sensor and guide wire assembly, wherein the external contour at the distal sensor portion exhibits a cross-section which is enlarged compared to a cross-section of the external contour proximal to the distal sensor portion that encompasses said fluid pressure sensor element.

2. A sensor and guide wire assembly according to claim 1, wherein the external contour at the distal sensor portion has a maximal cross-sectional dimension which is at least 10% larger than a maximal cross-sectional dimension of the external contour proximal to the distal sensor portion.

3. A sensor and guide wire assembly according to claim 2, wherein an external contour portion located distally of the distal sensor portion exhibits a maximal cross-sectional dimension which is smaller than said maximal cross-sectional dimension of said distal sensor portion.

4. A sensor and guide wire assembly according to claim 2, wherein an external contour portion located distally of the distal sensor portion exhibits a maximal cross-sectional dimension which is essentially equal to said maximal cross-sectional dimension of said distal sensor portion.

5. A sensor and guide wire assembly according to claim 1, wherein the external contour at the distal sensor portion has a circular cross-section.

6. A sensor and guide wire assembly according to claim 1, wherein the external contour at the distal sensor portion has a non-circular cross-section.

7. A sensor and guide wire assembly according to claim 2, wherein said maximal cross-sectional dimension of the external contour proximal to the distal sensor portion is 0.35 mm.

8. A sensor and guide wire assembly according to claim 2, wherein said maximal cross-sectional dimension of the external contour at the distal sensor portion is less than 2.0 mm.

9. A sensor and guide wire assembly according to claim 1, wherein said fluid pressure sensor element comprises circuitry for wireless communication of said measurement.

10. A sensor and guide wire assembly according to claim 1, wherein the guide wire further comprises a distal tip, a coil spring, a flexible distal tube, and a proximal tube, and wherein the housing, the distal tip, the coil spring, the flexible distal tube, and the proximal tube form the external contour.

11. A sensor and guide wire assembly according to claim 10, wherein the coil spring is attached to the distal tip, and extends to the housing, and wherein the housing is a jacket or sleeve.

12. A sensor and guide wire assembly according to claim 10, wherein the guide wire further comprises a core wire, and wherein the sensor element is mounted at a distal portion of the core wire.

13. A sensor and guide wire assembly according to claim 1, wherein the guide wire further comprises a core wire, and wherein the sensor element is mounted at a distal portion of the core wire.

14. A sensor and guide wire assembly according to claim 13, wherein the sensor element is mounted in a recess at the distal portion of the core wire.

15. A sensor and guide wire assembly according to claim 1, further comprising a catheter configured to be guided over the guide wire.

16. A sensor and guide wire assembly according to claim 15, wherein an inner diameter of the catheter corresponds to an outer diameter of the external contour proximal to the distal sensor portion.

17. A sensor and guide wire assembly according to claim 16, wherein the inner diameter of the catheter is smaller than an outer diameter of the external contour at the distal sensor portion.

18. A sensor and guide wire assembly for intravascular measurement of a physiological variable in a living body, comprising:

a guide wire comprising an external contour;

a fluid pressure sensor element located at a distal sensor portion of the guide wire, wherein the external contour at the distal sensor portion exhibits a cross-section which is enlarged compared to a cross-section of the external contour proximal to the distal sensor portion to encompass said fluid pressure sensor element; and a catheter configured to be guided over the guide wire, wherein an inner diameter of the catheter corresponds to an outer diameter of the external contour proximal to the distal sensor portion, and wherein the inner diameter of the catheter is smaller than an outer diameter of the external contour at the distal sensor portion.

19. A sensor and guide wire assembly according to claim 18, wherein a housing forms a portion of the external contour at the distal sensor portion of the guide wire, wherein the fluid pressure sensor element is encompassed by the housing and is at a radially internal location of the housing at the distal sensor portion, and wherein the housing comprises a window for establishing fluid communication between the sensor element and a medium surrounding the sensor and guide wire assembly.

* * * * *